United States Patent
Gressel et al.

(10) Patent No.: US 6,734,343 B1
(45) Date of Patent: May 11, 2004

(54) RHAMNOSYL-TRANSFERASE GENE AND USES THEREOF

(75) Inventors: Jonathan Gressel, Rehovot (IL); Yoram Eyal, Shimshon (IL); Robert Fluhr, Rehovot (IL)

(73) Assignees: Yeda Research and Development Co. Ltd., Rehovot (IL); Agricultural Research Organization, The Volcani Center, Beit Dagan (IL)

(*) Notice: Subject to any disclaimer, the term of this patent is extended or adjusted under 35 U.S.C. 154(b) by 0 days.

(21) Appl. No.: 09/889,738

(22) PCT Filed: Jan. 20, 2000

(86) PCT No.: PCT/IL00/00038

§ 371 (c)(1),
(2), (4) Date: Jul. 20, 2001

(87) PCT Pub. No.: WO00/43490

PCT Pub. Date: Jul. 27, 2000

(30) Foreign Application Priority Data

Jan. 22, 1999 (IL) .................................................. 128193

(51) Int. Cl.$^7$ .......................... A01H 5/00; C12N 15/09; C12N 15/11; C12N 15/52; C12N 15/82
(52) U.S. Cl. ...................... 800/286; 800/278; 800/284; 800/298; 536/23.1; 536/23.2; 536/23.6; 435/419; 435/468; 435/471; 435/483; 435/414; 435/252.3; 435/252.9; 435/254.21
(58) Field of Search ................................ 800/278, 284, 800/285, 286, 295, 316; 435/468, 419, 471, 252.3, 7.31, 7.32, 414, 252.9, 15, 254.21, 483; 536/23.1, 23.2, 23.6

(56) References Cited

PUBLICATIONS

Fourgoux–Nicol et al., 1999, Plant Molecular Biology, 40: 857–872.*
Elomaa P. et al., Molecular Breeding 1996, 2: 41–50.*
Waterhouse P. et al., Trends in Plant Sciences, Nov. 1999, vol. 4, No. 11 pp. 452–457.*
Smith C. et al.; Nature 1988, 334: 724–726.*
Luth D. et al. Plant, Cell, Tissue and Organ Culture, 57 (3): 219–222.*
Mok D. et al., GenBank Accession No. AF101972.*
Bar–Peled M. et al., J. of Biol. Chem., Nov. 5, 1991, vol. 266, No. 31, pp 20953–20959.*
Barber, G.A., "The Enzyme Synthesis Of Uridine Diphosphate L–Rhamnose", *Biochem. Biophys. Res. Commun*, 8(3):204–209, 1962.
Bar–Peled et al, "UDP– Rhamnose: Flavanone–7–O–glucoside–2–O– Rhamnosyl–transferse; Purification and Characterization of an Enzyme Catalyzing the Productions of Bitter Compounds in Citrus", *J. Biol. Chem.*, 266(31):20953–20959, 1991.
Berhow et al, "Biosynthesis of Naringin and Prunin in Detached Grapefruit", *Phytochemistry*, 28:1627–1630, 1989.
Castillo et al, "Naringin and Neohesperidin Levels During Development of Leaves, Flower Buds and Fruits of *Citrus Aurantium*", *Plant Physiol.*, 99:67–73, 1992.
Castillo et al, "7–O–glucoside and Prunin in Citrus Species (*C. Aurantium* and *C. Paradisi*). A Study of Their Quantataive Distribution in Immature Fruits and as Immediate Precursors of Neophesperidin and Naringen in *C. Auranium*", *J. Agric. Food Chem.*, 41:1920–1924, 1993.
Cooley et al, "Insertional Inactivation of the Tomato Polygalacteronase Gene", *Plant Mol. Biol.*, 38:521–530, 1998.
Guadagni et al, "Effect of Some Citrus Juice Constituents on Taste Thresholds for Limonin and Naringen Bitterness", *J. Sci. Fd. Agric.*, 24:1277–1288, 1973.
Horowitz et al, "Flavonoid Constituents of Citrus" in "Citrus Science and Technology", S. Nagy et al, eds. AVI Publishing Co., Westport, Conn. vol. 1, pp. 397–426, 1997.
Horowitz et al, "Dihydrochalcone Sweeteners From Citrus Flavorones in Alternative Sweeteners", Nabors et al, eds., Marcel Dekker, Inc. NY, pp 135–153, 1986.
Jimeno et al, "Use of Naringanase Immobilized on Glycophase–Coated Porous Glass for Fruit Juice Debittering", *Process Biochemistry*, pp. 13–16, Feb., 1987.
Lewinsohn et al, "Glucosylation of Exogenous Flavanones by Grapefruit (Citrus Paradisi) Cell Cultures", *Phytochemistry*, 25(11):2531–2535, 1986.
Matthews et al, "Removal of Limolin and Naringinmfrom Citrus Juice by Styrene Divinylbenzene Resins" *Food Tech.*, Apr., 1990, pp. 130–132.
McIntosh et al, "Biosynthesis of Naringin in *Citrus Paradisi*: UDP–glucosyl–transferase Activity in Grapefruit Seedlings", *Phytochemistry*, 29(5):1533–1538, 1990.
Miao et al, "Targeted Disruption of the TGA3 Locus in *Arabidopsis Thalania*", Plant J., 7(2):359–365, 1995.
Naim et al, "The Water–Sweet Aftertaste of Neohesperidin Dihydrochalcone and Thaumatin as a Method for Determining Their Sweet Persistence", *Chemical Senses*, 11(3):361–370, 1986.
Schaefer,BC, "Revolutions in Rapid Amplification of cDNA Ends: New Strategies for Polymerase Chain Reaction Cloning of Full–Length cDNA Ends", *Analytical Biochemistry*, 227:255–273, 1995.
Strepp et al, "Plant Nuclear Gene Knockout Reveals a Role in Plastid Division for the Homolog of the Bacterial Cell Division Protein FtsZ, an Ancestral Tubulin", *Proc. Natl. Acad. Sci. USA*, 95:4368–4373, 1998.

* cited by examiner

*Primary Examiner*—David T. Fox
*Assistant Examiner*—Russell Kallis
(74) *Attorney, Agent, or Firm*—G.E. Ehrlich (1995) Ltd.

(57) ABSTRACT

An isolated polynucleotide comprising a nucleotide sequence encoding a polypeptide having a flavanone-7-O-glucoside-2"-O-rhamnosyl-transferase catalytic activity and its uses.

35 Claims, 2 Drawing Sheets

Fig. 1

```
ATGGATACCAAGCATCAAGATAAGCCAAGCATTCTCATGTTACCATGGCTAGCTCATGGG  60
 M  D  T  K  H  Q  D  K  P  S  I  L  M  L  P  W  L  A  H  G
CACATAGCTCCACACCTTGAACTTGCCAAGAAGCTTTCACAGAAAAACTTCCACATATAT 120
 H  I  A  P  H  L  E  L  A  K  K  L  S  Q  K  N  F  H  I  Y
TTCTGCTCTACTCCCAACAATCTACAATCCTTCGGCAGAAATGTTGAAAAAACTTCTCA  180
 F  C  S  T  P  N  N  L  Q  S  F  G  R  N  V  E  K  N  F  S
TCTTCAATACAACTCATAGAACTGCAACTTCCCAATACATTCCCTGAACTTCCTTCACAA 240
 S  S  I  Q  L  I  E  L  Q  L  P  N  T  F  P  E  L  P  S  Q
AATCAGACCACAAAAAACCTTCCTCCCCATCTTATTTATACTCTCGTGGGAGCATTTGAA 300
 N  Q  T  T  K  N  L  P  P  H  L  I  Y  T  L  V  G  A  F  E
GACGCAAAACCTGCTTTTTGCAACATCTTGGAGACGCTTAAACCAACCCTTGTTATGTAT 360
 D  A  K  P  A  F  C  N  I  L  E  T  L  K  P  T  L  V  M  Y
GATTTGTTCCAACCGATGGCGGCGGAGGCAGCTTACCAGTATGACATAGCTGCTATTTTG 420
 D  L  F  Q  P  M  A  A  E  A  A  Y  Q  Y  D  I  A  A  I  L
TTCTTACCCTTATCTGCAGTAGCCTGCTCTTTCTTGCTGCACAATATCGTAAATCCCAGC 480
 F  L  P  L  S  A  V  A  C  S  F  L  L  H  N  I  V  N  P  S
CTGAAATACCCTTTCTTTGAATCTGATTACCAAGATAGAGAAAGCAAGAACATCAATTAC 540
 L  K  Y  P  F  F  E  S  D  Y  Q  D  R  E  S  K  N  I  N  Y
TTCCTGCATCTTACTGCCAATGGCACCTTAAACAAAGACAGGTTCTTAAAAGCTTTCGAA 600
 F  L  H  L  T  A  N  G  T  L  N  K  D  R  F  L  K  A  F  E
CTATCTTGCAAATTTGTGTTCATCAAAACATCAAGAGAGATTGAATCCAAGTACTTGGAT 660
 L  S  C  K  F  V  F  I  K  T  S  R  E  I  E  S  K  Y  L  D
TATTTTCCTTCTTTAATGGGAAATGAAATAATTCCAGTAGGGCCTCTAATCCAAGAACCT 720
 Y  F  P  S  L  M  G  N  E  I  I  P  V  G  P  L  I  Q  E  P
ACCTTCAAGGTAGATGATACAAAGATCATGGACTGGCTGAGCCAAAAGGAGCCTCGTTCA 780
 T  F  K  V  D  D  T  K  I  M  D  W  L  S  Q  K  E  P  R  S
GTCGTGTATGCATCCTTTGGCAGTGAGTACTTTCCTTCCACGGATGAAATACATGACATA 840
 V  V  Y  A  S  F  G  S  E  Y  F  P  S  T  D  E  I  H  D  I
CCTATTGGGTTATTGCTCACCGAGGTTAATTTTATATGGGCTTTCAGATTACATCCTGAT 900
 P  I  G  L  L  L  T  E  V  N  F  I  W  A  F  R  L  H  P  D
CAGAAAATCACCATACACGAACCACTCCCTCAGGGCTTTCCTCAGCACATTCAAAGGAAT 960
 E  K  M  T  I  E  E  A  L  P  Q  G  F  A  E  E  I  E  R  N
AATAAGGGAATGATAGTACAAGGTTGGGTTCCGCAGGCTAAAATTTTAAGGCATGGAAGC 1020
 N  K  G  M  I  V  Q  G  W  V  P  Q  A  K  I  L  R  H  G  S
ATCGGCGGATTTTTGAGTCATTGTGGTTGGGGCTCGGTGGTTGAGGGGATGGTTTTCGGG 1080
 I  G  G  F  L  S  H  C  G  W  G  S  V  V  E  G  M  V  F  G
GTACCAATCATAGGTGTGCCAATGGCATATGAGCAGCCAAGCAATGCCAAGGTGGTGGTT 1140
 V  P  I  I  G  V  P  M  A  Y  E  Q  P  S  N  A  K  V  V  V
GACAATGGTATGGGCATGGTCGTTCCAAGAGATAAGATCAATCAAAGACTTGGAGGAGAG 1200
 D  N  G  M  G  M  V  V  P  R  D  K  I  N  Q  R  L  G  G  E
GAGGTCGCGAGGGTCATTAAACATGTTGTGCTGCAAGAAGAAGCGAAGCAAATAAGAAGA 1260
 E  V  A  R  V  I  K  H  V  V  L  Q  E  E  A  K  Q  I  R  R
AAAGCTAATGAAATTAGTGAGAGTATGAAGAAGATACGGGACGCACAGATGAGTGTGGTG 1320
 K  A  N  E  I  S  E  S  M  K  K  I  G  D  A  Q  M  S  V  V
GTGGAGAAACTGCTGCAGCTTGTCAAGAAATCTGAATAA 1359
 V  E  K  L  L  Q  L  V  K  K  S  E  *
```

Fig. 2

SEQUENCE LISTING

```
<160> NUMBER OF SEQ ID NOS: 21

<210> SEQ ID NO 1
<211> LENGTH: 8
<212> TYPE: PRT
<213> ORGANISM: Citrus X paradisi

<400> SEQUENCE: 1
```

```
Asn Tyr Phe Leu His Leu Thr Ala
1               5

<210> SEQ ID NO 2
<211> LENGTH: 3
<212> TYPE: PRT
<213> ORGANISM: Citrus X paradisi

<400> SEQUENCE: 2

Tyr Pro Phe
1

<210> SEQ ID NO 3
<211> LENGTH: 7
<212> TYPE: PRT
<213> ORGANISM: Citrus X paradisi

<400> SEQUENCE: 3

Ile Ala Ala Ile Leu Phe Leu
1               5

<210> SEQ ID NO 4
<211> LENGTH: 8
<212> TYPE: PRT
<213> ORGANISM: Citrus X paradisi

<400> SEQUENCE: 4

Tyr Phe Pro Ser Leu Met Gly Asn
1               5

<210> SEQ ID NO 5
<211> LENGTH: 8
<212> TYPE: PRT
<213> ORGANISM: Citrus X paradisi

<400> SEQUENCE: 5

Glu Lys Met Thr Ile Glu Glu Ala
1               5

<210> SEQ ID NO 6
<211> LENGTH: 4
<212> TYPE: PRT
<213> ORGANISM: Citrus X paradisi

<400> SEQUENCE: 6

Leu Phe Gln Pro
1

<210> SEQ ID NO 7
<211> LENGTH: 14
<212> TYPE: PRT
<213> ORGANISM: Citrus X paradisi

<400> SEQUENCE: 7

Val Val Asp Asn Gly Met Gly Met Val Val Pro Arg Asp Lys
1               5                   10

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide
<221> NAME/KEY: misc_feature
<222> LOCATION: (9)..(9)
<223> OTHER INFORMATION: Modified base : Inosine
```

```
<221> NAME/KEY: misc_feature
<222> LOCATION: (15)..(15)
<223> OTHER INFORMATION: Modified base : Inosine

<400> SEQUENCE: 8
gayaayggna tgggnatggt                                                   20

<210> SEQ ID NO 9
<211> LENGTH: 7
<212> TYPE: PRT
<213> ORGANISM: Citrus X paradisi

<400> SEQUENCE: 9

Asp Asn Gly Met Gly Met Val
1               5

<210> SEQ ID NO 10
<211> LENGTH: 23
<212> TYPE: DNA
<213> ORGANISM: Artificial sequence
<220> FEATURE:
<223> OTHER INFORMATION: Synthetic oligonucleotide
<221> NAME/KEY: misc_feature
<222> LOCATION: (12)..(12)
<223> OTHER INFORMATION: Modified base: Inosine

<400> SEQUENCE: 10
garaaratga cnathgarga rgc                                               23

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide
<221> NAME/KEY: misc_feature
<222> LOCATION: (12)..(12)
<223> OTHER INFORMATION: Modified base : Inosine
<221> NAME/KEY: misc_feature
<222> LOCATION: (18)..(18)
<223> OTHER INFORMATION: Modified base : Inosine
<221> NAME/KEY: misc_feature
<222> LOCATION: (21)..(21)
<223> OTHER INFORMATION: Modified base : Inosine

<400> SEQUENCE: 11
aaytayttyc tncayctnac ngc                                               23

<210> SEQ ID NO 12
<211> LENGTH: 8
<212> TYPE: PRT
<213> ORGANISM: Citrus X paradisi

<400> SEQUENCE: 12

Asn Tyr Phe Leu His Leu Thr Ala
1               5

<210> SEQ ID NO 13
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 13
gttttcccag tcacgacgtt tttttttttt ttt                                    33
```

<210> SEQ ID NO 14
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 14
gttttcccag tcacgacg                                                 18

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
catgcccata ccattgtc                                                 18

<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 16
gacaatggta tgggcatg                                                 18

<210> SEQ ID NO 17
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 17
cctcaaccac cgagccccaa ccac                                          24

<210> SEQ ID NO 18
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 18
catctagaat ggataccaag catcaag                                       27

<210> SEQ ID NO 19
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 19
caggatcctt attcagattt cttgacaag                                     29

<210> SEQ ID NO 20
<211> LENGTH: 1359
<212> TYPE: DNA
<213> ORGANISM: Citrus X paradisi

<400> SEQUENCE: 20

-continued

```
atggatacca agcatcaaga taagccaagc attctcatgt taccatggct agctcatggg    60
cacatagctc cacaccttga acttgccaag aagctttcac agaaaaactt ccacatatat   120
ttctgctcta ctcccaacaa tctacaatcc ttcggcagaa atgttgaaaa aaacttctca   180
tcttcaatac aactcataga actgcaactt cccaatacat tccctgaact tccttcacaa   240
aatcagacca caaaaaacct tcctccccat cttatttata ctctcgtggg agcatttgaa   300
gacgcaaaac ctgcttttg caacatcttg gagacgctta aaccaaccct tgttatgtat   360
gatttgttcc aaccgatggc ggcggaggca gcttaccagt atgacatagc tgctattttg   420
ttcttaccct tatctgcagt agcctgctct ttcttgctgc acaatatcgt aaatcccagc   480
ctgaaatacc ctttctttga atctgattac caagatagag aaagcaagaa catcaattac   540
ttcctgcatc ttactgccaa tggcacctta aacaaagaca ggttcttaaa agctttcgaa   600
ctatcttgca aatttgtgtt catcaaaaca tcaagagaga ttgaatccaa gtacttggat   660
tattttcctt ctttaatggg aaatgaaata attccagtag ggcctctaat ccaagaacct   720
accttcaagg tagatgatac aaagatcatg gactggctga gccaaaagga gcctcgttca   780
gtcgtgtatg catcctttgg cagtgagtac tttccttcca cggatgaaat acatgacata   840
gctattgggt tattgctcac cgaggttaat tttatatggg ctttcagatt acatcctgat   900
gagaaaatga cgatagagga agcactgcct cagggctttg ctgaggagat tgaaaggaat   960
aataagggaa tgatagtaca aggttgggtt ccgcaggcta aaattttaag gcatggaagc  1020
atcggcggat ttttgagtca ttgtggttgg ggctcggtgg ttgaggggat ggttttcggg  1080
gtaccaatca taggtgtgcc aatggcatat gagcagccaa gcaatgccaa ggtggtggtt  1140
gacaatggta tgggcatggt cgttccaaga gataagatca atcaaagact tggaggagag  1200
gaggtggcga gggtcattaa acatgttgtg ctgcaagaag aagcgaagca aataagaaga  1260
aaagctaatg aaattagtga gagtatgaag aagataggg acgcacagat gagtgtggtg  1320
gtggagaaac tgctgcagct tgtcaagaaa tctgaataa                         1359
```

<210> SEQ ID NO 21
<211> LENGTH: 452
<212> TYPE: PRT
<213> ORGANISM: Citrus X paradisi

<400> SEQUENCE: 21

```
Met Asp Thr Lys His Gln Asp Lys Pro Ser Ile Leu Met Leu Pro Trp
 1               5                  10                  15

Leu Ala His Gly His Ile Ala Pro His Leu Glu Leu Ala Lys Lys Leu
             20                  25                  30

Ser Gln Lys Asn Phe His Ile Tyr Phe Cys Ser Thr Pro Asn Asn Leu
         35                  40                  45

Gln Ser Phe Gly Arg Asn Val Glu Lys Asn Phe Ser Ser Ile Gln
     50                  55                  60

Leu Ile Glu Leu Gln Leu Pro Asn Thr Phe Pro Glu Leu Pro Ser Gln
 65                  70                  75                  80

Asn Gln Thr Thr Lys Asn Leu Pro Pro His Leu Ile Tyr Thr Leu Val
                 85                  90                  95

Gly Ala Phe Glu Asp Ala Lys Pro Ala Phe Cys Asn Ile Leu Glu Thr
            100                 105                 110

Leu Lys Pro Thr Leu Val Met Tyr Asp Leu Phe Gln Pro Met Ala Ala
        115                 120                 125

Glu Ala Ala Tyr Gln Tyr Asp Ile Ala Ala Ile Leu Phe Leu Pro Leu
```

-continued

```
                130                 135                 140
Ser Ala Val Ala Cys Ser Phe Leu Leu His Asn Ile Val Asn Pro Ser
145                 150                 155                 160

Leu Lys Tyr Pro Phe Phe Glu Ser Asp Tyr Gln Asp Arg Glu Ser Lys
                165                 170                 175

Asn Ile Asn Tyr Phe Leu His Leu Thr Ala Asn Gly Thr Leu Asn Lys
                180                 185                 190

Asp Arg Phe Leu Lys Ala Phe Glu Leu Ser Cys Lys Phe Val Phe Ile
                195                 200                 205

Lys Thr Ser Arg Glu Ile Glu Ser Lys Tyr Leu Asp Tyr Phe Pro Ser
        210                 215                 220

Leu Met Gly Asn Glu Ile Ile Pro Val Gly Pro Leu Ile Gln Glu Pro
225                 230                 235                 240

Thr Phe Lys Val Asp Asp Thr Lys Ile Met Asp Trp Leu Ser Gln Lys
                245                 250                 255

Glu Pro Arg Ser Val Val Tyr Ala Ser Phe Gly Ser Glu Tyr Phe Pro
                260                 265                 270

Ser Thr Asp Glu Ile His Asp Ile Ala Ile Gly Leu Leu Leu Thr Glu
        275                 280                 285

Val Asn Phe Ile Trp Ala Phe Arg Leu His Pro Asp Glu Lys Met Thr
        290                 295                 300

Ile Glu Glu Ala Leu Pro Gln Gly Phe Ala Glu Glu Ile Glu Arg Asn
305                 310                 315                 320

Asn Lys Gly Met Ile Val Gln Gly Trp Val Pro Gln Ala Lys Ile Leu
                325                 330                 335

Arg His Gly Ser Ile Gly Gly Phe Leu Ser His Cys Gly Trp Gly Ser
                340                 345                 350

Val Val Glu Gly Met Val Phe Gly Val Pro Ile Ile Gly Val Pro Met
        355                 360                 365

Ala Tyr Glu Gln Pro Ser Asn Ala Lys Val Val Val Asp Asn Gly Met
        370                 375                 380

Gly Met Val Val Pro Arg Asp Lys Ile Asn Gln Arg Leu Gly Gly Glu
385                 390                 395                 400

Glu Val Ala Arg Val Ile Lys His Val Val Leu Gln Glu Glu Ala Lys
                405                 410                 415

Gln Ile Arg Arg Lys Ala Asn Glu Ile Ser Glu Ser Met Lys Lys Ile
                420                 425                 430

Gly Asp Ala Gln Met Ser Val Val Val Glu Lys Leu Leu Gln Leu Val
        435                 440                 445

Lys Lys Ser Glu
        450
```

RHAMNOSYL-TRANSFERASE GENE AND USES THEREOF

FIELD AND BACKGROUND OF THE INVENTION

The present invention relates to a nucleic acid encoding a 1-2-rhamnosyl-transferase and uses thereof. More particularly, the present invention relates to a multistep process of converting hesperidin from orange peels to the sweetener neohesperidin dihydrochalcone (NHDC), in which, in one of the steps, 1-2-rhamnosyl-transferase in the presence of activated rhamnose is used in a rhamnosylation reaction to convert hesperidinase-treated hesperidin (H7G) to neohesperidin. Further particularly, the present invention relates to genetically modified plants of the Citrus genus including an antisense or sense (for co-suppression) construct which comprises the above nucleic acid or a gene knock-out integrated construct to provide less bitter grapefruits, pomelos and other citrus containing bitter flavanoid glycosides.

The bitter flavanones naringin and neohesperidin (FIG. 1) are produced only in young leaves and fruits of a few citrus species, such as grapefruit and pomelo, accumulate in a brief few week period, and remain through maturity (Castillo et al., 1992). Isomerically structured, yet tasteless flavanones, such as hesperidin (FIG. 1) are produced in oranges at the same time in development (Castillo et al., 1993). The differences between the tastelessness of orange hesperidin and the bitterness of grapefruit and pomelo naringin and neohesperidin depend on a specific set of glycosylation reactions (glucosylation and rhamnosylation) as further detailed hereinunder.

Low consumption of grapefruit is due in part to the bitter flavor of its juice and flesh (Matthews et al., 1990). This bitterness is due to the presence of large amounts of the flavanone glycoside naringin, as well as limonin in the juice. While limonin is a problem limited to the juice (Guadagni et al., 1973), in the intact fruit it appears in the tasteless A ring monolactone and forms the bitter dilactone only after maceration in the acidic juice environment (Matthews et al., 1990).

Thus, bitterness in the fruit can be decreased by reducing naringin levels. The bitterness in commercially prepared grapefruit juice is presently diminished to levels more acceptable by consumers by using resins that adsorb some bitter compounds or by treating the juice with the immobilized enzyme naringinase (Jimeno et al., 1987; Nikdel et al., 1989).

Commercial naringinase preparations typically consist of two enzymes, mainly α-rhamnosidase and some β-glucosidase, which successively hydrolyze one or both the sugar groups from naringin, leaving the tasteless compound prunin (naringenin-7-O-glucoside). Removal of the terminal rhamnose removes about 95% of the bitterness. Evidently, this procedure does not solve the problem of bitterness of whole fruit or home prepared juice.

A better approach which also addresses the above problem would, therefore, be to regulate the levels of naringin within the plant itself.

However, because of high heterozygousity of the commercial citrus varieties, classical plant breeding programs, will be hard put to yield identical varieties, yet having significantly less bitter fruit by reducing naringin. It will be appreciated in this respect that the presently available low naringin varieties (such as the Texas Red) are also low yielding.

While reducing the present invention to practice, studies of the naringin flavonoid metabolism (see below) assisted (i) in developing novel approaches to the problem; (ii) to further study the critical glycosylation steps that produce naringin; and (iii) in using this knowledge to modulate the degree of bitterness.

Figure 1:
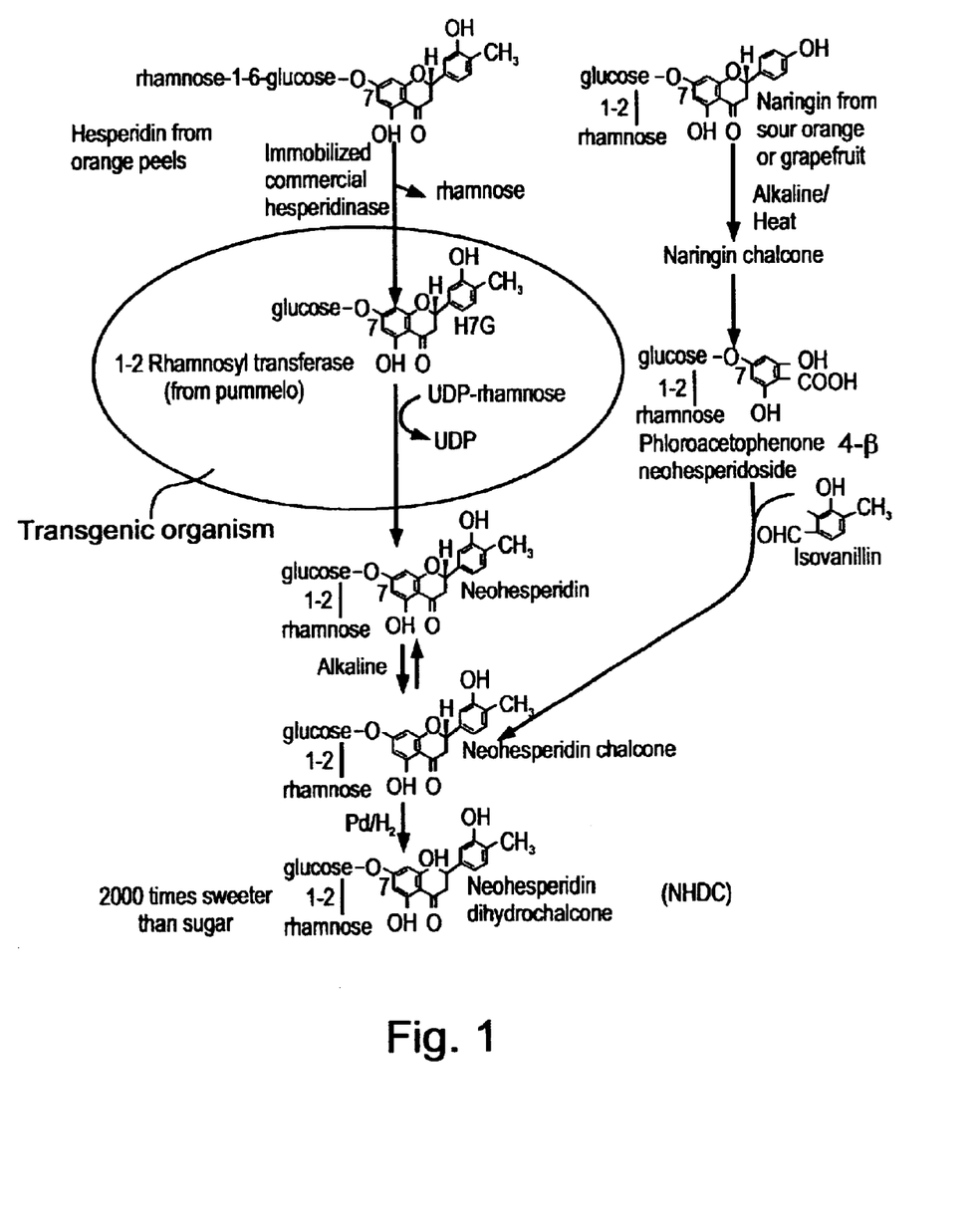
FIG. 1 depicts a prior art process (right path) and a process according to the present invention (left path) of producing the sweetener NHDC.

Citrus flavonoids ubiquity and biosynthesis: The genus Citrus contains many flavonoid glycosides that differ either in the structure of the aglycone or their sugar moieties. The major flavonoid in pomelo and grapefruit peel is naringin, while sweet orange peel contains hesperidin (Horowitz and Gentili, 1977 and FIG. 1). Peels of sour orange, trifoliate orange and Ponderosa lemon contain neohesperidin (FIG. 1). Neohesperidin and naringin are flavanone glycosides that contain the same disaccharide, β-neohesperidose (2-O-α-L-rhamnosyl-β-D-glucose), which is attached at position C-7 of different aglycones, hesperetin and naringenin, respectively. Hesperidin and narirutin are isomers, respectively, of the above compounds that contain the disaccharide rutinose (6-O-α-L-rhamnosyl-β-D-glucose).

These flavonoids have some remarkable taste properties. Naringin and neohesperidin are extremely bitter, while narirutin and hesperidin are nearly tasteless (Horowitz and Gentili, 1986; Naim et al., 1986).

Flavonoids in Citrus: The highest naringin levels are associated with very young developing leaves and fruit tissue. Undifferentiated cells of *Citrus paradisi* (grapefruit) were able to biotransform exogenous naringenin and hesperetin, into prunin (naringenin-7-O-glucoside) and hesperetin-7-O-glucose (H-7-G), respectively. Further 1-2-rhamnosylation resulting in naringin or neohesperidin synthesis was not detected, although 1-6-rhamnosylation resulting in narirutin was observed (Lewinsohn et al., 1986, 1989b).

All of the above suggests that the blockage in the stepwise production of the naringenin from prunin (naringenin-7-O-glucoside) in the undifferentiated Citrus cells is caused by the absence of a specific rhamnosyl transferase activity.

Lewinsohn et al. detected chalcone-synthase and UDP-glucose, flavanone-7-O-glucosyl-transferase activities in cell-free extracts of Citrus (Lewinsohn et al. 1989a). Partial purification of the glucosyl transferase has been recently reported and some of its characteristics are therefore known (McIntosh and Mansell, 1989).

The glucosylated flavanone was further rhamnosylated. Chalcone-synthase activity was detected in cell-free extracts derived from young leaves and fruits.

Young fruits (2 millimeter diameter) had the highest chalcone synthase activity. In earlier studies it was shown that the glycosylation of the aglycone, naringenin, in undifferentiated Citrus cells occurs in two steps. First there was an initial glucosylation resulting in prunin (Lewinsohn et al. 1986, 1989b), and then a further rhamnosylation of prunin occurred when exogenous UDP-glucose and NADPH were added to the extract forming the end-product naringin (Lewinsohn et al 1989b).

Prunin was also shown to be a likely intermediate in the biosynthesis of naringin in immature grapefruit fruits (Berhow and Vandercook 1989).

Several glucosyl-transferases from plants catalyze the transfer of the sugar moiety from an activated UDP-sugar to a specific site on the flavonoids (Hahlbrock, 1981). Enzymatic preparations from plants catalyze the conversion of UDP-glucose to UDP-rhamnose in the presence of NADPH (Barber, 1962). The conversion is due to at least three different enzymatic activities requiring NADH or NADPH.

It was not previously known how this conversion is catalyzed in Citrus. A coupled assay using UDP-glucose with NADPH was developed, which formed a rhamnosylated flavanone glycoside, indicative of a UDP-rhamnose:flavanone-7-O-glucoside-2'-O-rhamnosyl-transferase activity (α-1-2 rhamnosyl transferase). A system was thereafter developed to directly biosynthesize radiolabeled UDP-rhamnose from [$^{14}$C]-UDP glucose and NADPH for use in direct assay of the α-1-2 rhamnosyl transferase activity during purification of the α-1-2 rhamnosyl transferase. The direct assay facilitated the purification of the α-1-2 rhamnosyl transferase. Once both rhamnosyl transferase substrates were available it was possible to purify the enzyme. Purity to homogeneity of the α-1-2 rhamnosyl transferase in a four step procedure, which includes S-200 gel filtration, affinity column, ion exchange-FPLC and reverse-phase HPLC (Bar-Peled et al. 1991) was achieved and an antibody to it was elicited. These findings allowed to isolate the gene, which is the subject of this invention.

Semi-artificial sweetener: Neohesperidin and naringin from the peels of sour oranges and grapefruits are being converted into neohesperidin dihydrochalcone (NHDC), an intense sweetener used in the EU that is 2,000 fold sweeter than sugar (see right path on FIG. 1). NHDC is especially useful when long-lasting sweetness is desired, such as in chewing gum or in admixture with one of the artificial sweeteners. Currently, world-wide production of this NHDC is limited by the amount of neohesperidin and naringin available from these lesser grown Citrus species (less than 10% of total Citrus cultivated).

Unfortunately, the vast majority of citrus processed (oranges) contain large amounts of the hesperidin, an isomer having the terminal rhamnose attached by a 1→6 linkage instead of the 1→2 linkage. Hesperidin cannot be converted to the sweetener and is currently a waste by-product.

There is thus a widely recognized need for, and it would be highly advantageous to have, a nucleic acid encoding a 1-2-rhamnosyl-transferase to effect a multistep process of converting hesperidin from orange peels to the sweetener neohesperidin dihydrochalcone (NHDC), and to provide genetically modified plants of the Citrus genus including an antisense or sense (for co-suppression) construct thereof, or knock-out integrated construct, to provide less bitter grapefruits, pomelos and other citrus containing bitter flavanoid glycosides.

SUMMARY OF THE INVENTION

While reducing the present invention to practice, a novel rhamnosyl transferase gene from citrus responsible for producing the bitter flavanoids naringin and neohesperidin was isolated, sequenced, and characterized. This gene can be used in antisense or overproducing sense constructs to decrease the bitterness in grapefruit, and in sense constructs as part of the bioconversion of hesperidin from orange waste products to neohesperidin, used for the production of neohesperidin dihydrochalcone (NHDC), a sweetener. A knock-out construct can be used to knock-out the endo rhamnosyl transferase gene.

Thus, according to one aspect of the present invention there is provided an isolated polynucleotide comprising a nucleotide sequence encoding a polypeptide having a flavanone-7-O-glucoside-2"-O-rhamnosyl-transferase catalytic activity.

According to another aspect of the present invention there is provided a cell genetically modified to include, in an expressible sense orientation, a nucleotide sequence encoding a flavanone-7-O-glucoside-2"-O-rhamnosyl-transferase.

According to still another aspect of the present invention there is provided a plant cell of a plant species naturally expressing a flavanone-7-O-glucoside-2"-O-rhamnosyl-transferase messenger RNA, wherein the plant cell is genetically modified to include, in an expressible antisense orientation, a nucleotide sequence encoding an antisense RNA molecule being capable of in vivo base pairing with the flavanone-7-O-glucoside-2"-O-rhamnosyl-transferase messenger RNA, to thereby render the flavanone-7-O-glucoside-2"-O-rhamnosyl-transferase messenger RNA, when expressed, amenable to degradation by nucleases present in the plant cell.

According to yet another aspect of the present invention there is provided a transgenic plant of a species naturally expressing a flavanone-7-O-glucoside-2"-O-rhamnosyl-transferase messenger RNA, wherein the transgenic plant is genetically modified to include, in an expressible antisense orientation, a nucleotide sequence encoding an antisense RNA molecule being capable of in vivo base pairing with the flavanone-7-O-glucoside-2"-O-rhamnosyl-transferase messenger RNA, to thereby render the flavanone-7-O-glucoside-2"-O-rhamnosyl-transferase messenger RNA, when expressed, amenable to degradation by nucleases present in the transgenic plant.

According to a further aspect of the present invention there is provided a plant cell of a plant species naturally expressing a flavanone-7-O-glucoside-2"-O-rhamnosyl-transferase, wherein the plant cell is genetically modified to include, in an overexpressible sense orientation, a nucleotide sequence encoding a sense RNA molecule being capable of inducing a co-suppression effect to thereby reduce production of the flavanone-7-O-glucoside-2"-O-rhamnosyl-transferase in the plant cell.

According to yet a further aspect of the present invention there is provided a transgenic plant of a species naturally expressing a flavanone-7-O-glucoside-2"-O-rhamnosyl-transferase, the plant is genetically modified to include, in an overexpressible sense orientation, a nucleotide sequence encoding a sense RNA molecule being capable of inducing a co-suppression effect to thereby reduce production of the flavanone-7-O-glucoside-2"-O-rhamnosyl-transferase in the plant cell.

According to still a further aspect of the present invention there is provided a transgenic plant or cell of a plant species naturally expressing a flavanone-7-O-glucoside-2"-O-rhamnosyl-transferase, the transgenic plant or cell being genetically modified to knock-out a gene encoding said flavanone-7-O-glucoside-2"-O-rhamnosyl-transferase to thereby abolish production of said flavanone-7-O-glucoside-2"-O-rhamnosyl-transferase in the transgenic plant or cell.

According to an additional aspect of the present invention there is provided a commercial process of producing neohesperidin comprising the steps of: (a) extracting hesperidin from a hesperidin producing species of the genus Citrus; (b) treating the hesperidin with a hesperidinase, thereby obtaining hesperetin-7-glucoside; and (c) treating the hesperetin-7-glucoside with a flavanone-7-O-glucoside-2"-O-rhamnosyl-transferase in the presence of activated rhamnose, thereby obtaining neohesperidin.

According to yet another additional aspect of the present invention there is provided a method of modifying a rhamnose-1-6-glucose linkage of a chemical compound to a rhamnose-1-2-glucose linkage comprising the steps of: (a) enzymatically treating the chemical compound to remove a rhamnose group thereof, thereby obtaining a first derivative of said chemical compound having a terminal glucose group; and (b) enzymatically treating the first derivative with recombinant flavanone-7-O-glucoside-2"-O-rhamnosyl-transferase in the presence of activated rhamnose, thereby obtaining a second derivative chemical compound having the rhamnose-1-2-glucose linkage.

According to one further aspect of the present invention there is provided a commercial process of producing neohesperidin dihydrochalcone comprising the steps of: (a) extracting hesperidin from a hesperidin producing species of the genus Citrus; (b) treating the hesperidin with a hesperidinase, thereby obtaining hesperetin-7-glucoside; (c) treating the hesperetin-7-glucoside with a flavanone-7-O-glucoside-2"-O-rhamnosyl-transferase in the presence of activated rhamnose, thereby obtaining neohesperidin; (d) treating the neohesperidin with an alkali, thereby obtaining neohesperidin chalcone; and (e) reducing the neohesperidin chalcone, thereby obtaining neohesperidin dihydrochalcone.

The present invention successfully addresses the shortcomings of the presently known configurations by providing a nucleic acid encoding a 1-2-rhamnosyl-transferase to effect a multistep process of converting hesperidin from orange peels to the sweetener neohesperidin dihydrochalcone (NHDC), and to provide genetically modified plants of the Citrus genus to provide less bitter grapefruits, pomelos and other citrus containing bitter flavanoid glycosides.

BRIEF DESCRIPTION OF THE DRAWINGS

The invention is herein described, by way of example only, with reference to the accompanying drawings, wherein:

FIG. 2 shows the sequence of the coding strand of a 1-2-rhamnosyl-transferase cDNA according to the present invention, and its translation into a protein shown in single letter code.

DESCRIPTION OF THE PREFERRED EMBODIMENTS

The present invention is of a 1-2-rhamnosyl-transferase gene and the recombinant protein product hereof, which can be used in a multistep process of converting hesperidin from orange peels to the sweetener neohesperidin dihydrochalcone (NHDC), and in providing genetically modified plants of the genus Citrus characterized by lowered bitterness.

The principles and operation of the present invention may be better understood with reference to the drawings and accompanying descriptions.

Before explaining at least one embodiment of the invention in detail, it is to be understood that the invention is not limited in its application to the details of construction and arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. Generally, the nomenclature used herein and the laboratory procedures in recombinant DNA technology described below are those well known and commonly employed in the art.

While reducing the present invention to practice, a polynucleotide was isolated, having a nucleotide sequence encoding a polypeptide having a flavanone-7-O-glucoside-2"-O-rhamnosyl-transferase catalytic activity. The isolation of the flavanone-7-O-glucoside-2"-O-rhamnosyl-transferase gene was not at all trivial. Repeated attempts to isolate the gene via screening of either conventional cDNA libraries or expression cDNA libraries using oligonucleotides as well as antibodies raised against purified flavanone-7-O-glucoside-2"-O-rhamnosyl-transferase failed to yield positive clones. The successful approach of isolating the flavanone-7-O-glucoside-2"-O-rhamnosyl-transferase gene, which included reverse transcriptase polymerase chain reaction (RT-PCR) using degenerate primers followed by rapid amplification of cDNA ends (RACE), is further described in the Examples section that follows.

Having the cDNA in hand, screening of genomic libraries can readily be performed for isolating a genomic clone including a polynucleotide having introns and exons, the exons of which correspond to the cDNA sequence or parts thereof, and encode for flavanone-7-O-glucoside-2"-O-rhamnosyl-transferase. Both the complementary and genomic polynucleotides according to the present invention can be used to direct the synthesis of a messenger RNA (mRNA) encoding flavanone-7-O-glucoside-2"-O-rhamnosyl-transferase.

According to a preferred embodiment of the present invention, the isolated polynucleotide, either in its cDNA or genomic DNA form, wholly or partially synthetic (the term "isolated" may encompass all these possibilities) is ligated to a vector, preferably, an expression vector, either in sense or antisense orientation. The vector preferably selected is propagatable in plant cells and/or in microorganism cells, such as in bacteria. The vector can be of a type capable of directing the integration of sequences thereof into the genome of the recipient cell. Thus, within the cell, the nucleic acid may be incorporated, or not, within a chromosome. There may be more than one nucleotide sequence per haploid genome. This, for example, enables increased expression. A vector comprising a polynucleotide according to the present invention need not include a promoter, particularly if the vector is to be used to introduce the nucleic acid into cells for recombination into the genome.

However, as further detailed hereinunder, a promoter is preferably included in the vector.

The present invention also encompasses the expression product of any of the nucleic acid sequences disclosed and methods of making the expression product by expression from encoding nucleic acid therefor under suitable conditions in suitable host cells. Those skilled in the art are well able to construct vectors and design protocols for expression and recovery of products of recombinant gene expression.

Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning*: a Laboratory Manual: 2nd edition, Sambrook et al. 1989, Cold Spring Harbor Laboratory Press. Transformation procedures depend on the host used, but are well known. Many known techniques and protocols for manipulation of nucleic acids, for example, in preparation of nucleic acid constructs, mutagenesis, sequencing, introduction of DNA into cells and gene expression, and analysis of proteins are described in detail in *Short Protocols in Molecular Biology*, Second Edition, Ausubel et al. ed., John Wiley & Sons, 1992. The disclosures of Sambrook et al. and Ausubel et al. are incorporated herein by reference.

According to one embodiment of the present invention the nucleotide sequence is as set forth in SEQ ID NO:20 or a functional part thereof. By functional part it is meant a part capable of directing the synthesis of a polypeptide having a flavanone-7-O-glucoside-2"-O-rhamnosyl-transferase catalytic activity.

According to another embodiment of the present invention the nucleotide sequence shares between 50 and 100%, preferably between 60 and 100%, more preferably between 70 and 100%, yet more preferably between 80 and 100%, still more preferably between 90 and 100% identical bases with SEQ ID NO:20 or a functional part thereof, as determined using a sequence analysis software package developed by the Genetic Computer Group (GCG) at the University of Wisconsin with gap creation penalty of 50 and gap extension penalty of 3, provided that the nucleotide sequence encodes a polypeptide having a flavanone-7-O-glucoside-2"-O-rhamnosyl-transferase catalytic activity.

According to yet another preferred embodiment of the present invention, the nucleotide sequence is hybridizable with SEQ ID NO:20 or a functional part thereof under stringent hybridization, moderate hybridization or mild hybridization, wherein stringent hybridization is effected by a hybridization solution of 6×SSC and 1% SDS, hybridization temperature of 65° C., final wash solution of 0.1×SSC and final wash at 60° C., moderate hybridization is effected by a hybridization solution of 6×SSC and 1% SDS, hybridization temperature of 58° C., final wash solution of 0.5× SSC and final wash at 50° C., whereas mild hybridization is effected by a hybridization solution of 6×SSC and 1% SDS, hybridization temperature of 50° C., final wash solution of 2×SSC and final wash at 40 ° C. Thus, a hybridization according to the present invention is effected by a hybridization solution of 6×SSC and 1% SDS, hybridization temperature of 50–65° C., final wash solution of 0.1–2.0×SSC and final wash at 40–60° C.

According to a preferred embodiment of the present invention, the nucleotide sequence encodes a polypeptide as set forth in SEQ ID NO:21 or a functional part thereof. However, the polypeptide encoded by the nucleotide sequence of the present invention can share between 20 and 100%, preferably between 60 and 100%, more preferably between 70 and 100%, yet more preferably between 80 and 100%, still more preferably between 90 and 100% identical or conserved amino acids with SEQ ID NO:21 or a functional part thereof, as determined using a sequence analysis software package developed by the Genetic Computer Group (GCG) at the University of Wisconsin with gap creation penalty of 12 and gap extension penalty of 4, provided that the polypeptide has a flavanone-7-O-glucoside-2"-O-rhamnosyl-transferase catalytic activity.

A polynucleotide according to various aspects of the present invention may have the sequence of a flavanone-7-O-glucoside-2"-O-rhamnosyl-transferase gene or be a mutant, variant, derivative or allele of the sequence provided. Preferred mutants, variants, derivatives and alleles are those which encode a product (RNA or polypeptide) which retains a functional characteristic of the product encoded by the wild-type gene. Changes to a sequence, to produce a mutant, variant or derivative, may be by one or more of addition, insertion, deletion or substitution of one or more amino acids in an encoded polypeptide product. Of course, changes to the nucleic acid which make no difference to the encoded amino acid sequence are included.

In a preferred embodiment of the present invention a polynucleotide molecule comprises a nucleotide sequence which encodes an amino acid sequence shown in SEQ ID NO:21. The nucleotide sequence may comprise an encoding sequence shown in SEQ ID NO:20 or may be a mutant, variant, derivative or allele thereof encoding the same amino acid sequence, or a sequence which retains a functional characteristic of the product encoded by the wild-type gene.

Sequences comprising changes to or differences from the sequences shown may also be employed in the present invention, as discussed herein.

According to a preferred embodiment of the present invention the nucleotide sequence originates from a species of the genus Citrus, such as grapefruit and pomelo.

The nucleotide sequence information provided herein or any part thereof may be used in a data-base search to find homologous sequences, expression products of which can be tested for flavanone-7-O-glucoside-2"-O-rhamnosyl-transferase activity.

A further aspect of the present invention provides a method of identifying and cloning a flavanone-7-O-glucoside-2"-O-rhamnosyl-transferase gene homolog from a plant species other than pomelo which method employs a nucleotide sequence derived from SEQ ID NO:20. Nucleic acid libraries may be screened using techniques well known to those skilled in the art and homologous sequences thereby identified then tested. Hybridization may involve probing nucleic acid and identifying positive hybridization under suitable stringent conditions (in accordance with known techniques) and/or use of oligonucleotides as primers in a method of nucleic acid amplification, such as PCR. For probing, preferred conditions are those which are stringent enough for there to be a simple pattern with a small number of hybridizations identified as positive which can be investigated further. It is well known in the art to increase stringency of hybridization gradually until only a few positive clones remain. As an alternative to probing, though still employing nucleic acid hybridization, oligonucleotides designed to amplify DNA sequences may be used in PCR reactions or other methods involving amplification of nucleic acid, using routine procedures. See for instance "PCR protocols; A Guide to Methods and Applications", Eds. Innis et al. 1990, Academic Press, New York. Assessment of whether or not such a PCR product corresponds to a flavanone-7-O-glucoside-2"-O-rhamnosyl-transferase may be conducted in various ways. A PCR band from such a reaction might contain a complex mix of products. Individual products may be cloned and each one individual product may be cloned and each one individually screened. It may be analyzed by transformation to assess function on introduction into a plant of interest.

Thus, included within the scope of the present invention are polynucleotide molecules which encode amino acid sequences which are homologs of flavanone-7-O-glucoside-2"-O-rhamnosyl-transferase of pomelo. Homology may be at the nucleotide sequence and/or amino acid sequence level. Preferably, the nucleic acid or amino acid sequence of a homolog, or a mutant, allele, derivative or variant (see above) shares homology with SEQ ID NOs:20 or 21, respectively, preferably at least about 50%, or at least about 60%, or at least about 70%, or at least about 75%, or at least about 80% homology, most preferably at least about 90% homology, and the encoded product shares a phenotype with the flavanone-7-O-glucoside-2"-O-rhamnosyl-transferase gene. "Homology" may be understood to refer to similarity, in functional terms, in an amino acid sequence, as is standard in the art. Thus, for example, a % similarity figure will include amino acid differences that have little or no functional significance, such as leucine to isoleucine. Otherwise, homology may be taken to refer to identity. These definitions are further elaborated hereinabove. Thus, for example, gene homologs from other members of the genus Citrus may be identified.

In certain embodiments, an allele, variant, derivative, mutant or homolog of the specific sequence may show little overall homology, say about 20% or about 25%, or about 30%, or about 35% or about 40% or about 45%, with the specific sequence. However, in functionally significant domains or regions the amino acid homology may be much higher. Deletion mutagenesis, for example, may be used to test the function of a region of the polypeptide and its role in or necessity for catalytic activity.

Also according to the invention there is provided a plant cell having incorporated into its genome a sequence of nucleotides as provided by the present invention, under operative control of a promoter for control of expression of the encoded polypeptide. A further aspect of the present invention provides a method of making such a plant cell involving introduction of a vector comprising the sequence of nucleotides into a plant cell and causing or allowing recombination between the vector and the plant cell genome to introduce the sequence of nucleotides into the genome.

The present invention further encompasses a plant comprising a plant cell comprising nucleic acid according to the present invention e.g., as a result of introduction of the nucleic acid into the cell or an ancestor thereof, and selfed or hybrid progeny and any descendant of such a plant, also any part or propagule of such a plant, progeny or descendant, including sexually or apomictically obtained seed and vegetatively propagated plant material.

The principal characteristics which may be altered using the present invention are controlling the bitterness of fruits of plants of the genus Citrus as further detailed hereinunder. Over-expression of the gene product of the flavanone-7-O-glucoside-2"-O-rhamnosyl-transferase gene may lead to either bitterer fruits or less bitter fruits via a co-suppression mechanism; under-expression may lead to less bitter fruits. Down-regulation may be achieved, for example, with "gene silencing" techniques such as anti-sense or sense regulation, discussed further below. It can also be achieved with gene knockout.

This degree of control is useful to provide fruits of desired bitterness which can be used in the fresh fruit market or in the juice production industry, diminishing the need for de-bittering processes.

In preparing a vector according to the present invention various DNA fragments may be manipulated as necessary to create the desired vector or construct. This includes using linkers or adaptors as necessary to form suitable restriction sites or to eliminate unwanted restriction sites or other like manipulations which are known to those of ordinary skill in the art.

Promoters which are known or found to cause transcription of a selected gene in plant cells can be used in the present invention. Such promoters may be obtained from plants, plant pathogenic bacteria or plant viruses, and include, but are not necessarily limited to, the 35S and 19S promoters of cauliflower mosaic virus (CaMV35S and CaMV19S), the full-length transcript promoter from the figwort mosaic virus (FMV35S) and promoters isolated from plant genes such as EPSP synthase and ssRUBISCO genes, and promoters obtained from T-DNA genes of *Agrobacterium tumefaciens*, such as nopaline and mannopine synthases. The particular promoter selected should be capable of causing sufficient expression of sense or antisense RNA.

Particularly useful promoters for use in the present invention are fruit specific promoters which are expressed, for example, during ethylene production in the fruit and the full-length transcript promoter from the figwort mosaic virus (FMV35S). The FMV35S promoter is particularly useful because of its ability to cause uniform and high levels of expression.

The DNA sequence of a FMV35S promoter is presented in U.S. Pat. No. 5,512,466 and is identified as SEQ ID NO:17 therein. Examples of fruit specific promoters include the E8, E4, E17 and J49 promoters from tomato (Lincoln, J. and Fischer, R. (1988). Diverse mechanisms for the regulation of ethylene-inducible gene expression. Mol Gen Genet 212, 71–75), as well as the 2A11 promoter as described in U.S. Pat. No. 4,943,674.

As used herein, the term "CaMV35S" or "FMV35S" promoter include variations of these promoters, e.g., promoters derived by means of ligation with operator regions, random or controlled mutagenesis, addition or duplication of enhancer sequences, etc.

A 3' non-translated region is preferably included in a sense vector according to the present invention and includes a polyadenylation signal which functions in plants to cause the addition of polyadenylated nucleotides to the 3' end of a sense RNA sequence. Examples of suitable 3' regions are the 3' transcribed, non-translated regions containing the. polyadenylation signal of the tumor-inducing (Ti) plasmid genes of Agrobacterium, such as the nopaline synthase (NOS) gene, and plant genes like the 7S soybean storage protein genes and the pea E9 small subunit of the RuBP carboxylase gene (ssRUBISCO).

A sense RNA produced by a vector of the present invention also preferably contains a 5' non-translated leader sequence. This sequence can be derived from the promoter selected to express the gene, and can be specifically modified so as to increase translation of the sense RNA. The 5' non-translated regions can also be obtained from viral RNA's, from suitable eukaryotic genes, or from a synthetic gene sequence. The present invention is not limited to vector constructs wherein the non-translated region is derived from the 5' non-translated sequence that accompanies the promoter sequence. Rather, the non-translated leader sequences can be part of the 5' end of the non-translated region of the native coding sequence, or part of the promoter sequence, or can be derived from an unrelated promoter or coding sequence.

In a preferred embodiment according to the present invention, the vector that is used to introduce the sense or antisense RNA into the host cells or plants will comprise an appropriate selectable marker. In a more preferred embodiment according to the present invention the vector is a plant expression vector comprising both a selectable marker and an origin of replication. In another most preferred embodiment according to the present invention the vector will be a shuttle vector, which can propagate both in *E. coli* (wherein the construct comprises an appropriate selectable marker and origin of replication) and be compatible for propagation or integration in the genome of the organism of choice. In yet another embodiment, the construct comprising the promoter of choice and the gene of interest is placed in a viral vector which is used to infect the cells. This virus may be integrated in the genome of the organism of choice or may remain non-integrated.

The promoter of choice that is used in conjunction with this invention will comprise any suitable promoter as further detailed herein. It will be appreciated by one skilled in the art, however, that it is necessary to make sure that the transcription start site(s) will be located upstream of the open reading frame. In a preferred embodiment of the present invention, the promoter that is selected will comprise an element that is active in the particular host plant cells of interest.

These elements may be selected from transcriptional regulators that activate the transcription of genes essential for the survival of these cells in conditions of stress or starvation, including the heat shock proteins. Promoters containing this type of sequence may advantageously be used according to the present invention.

As further detailed hereinabove, DNA sequences encoding the translational start site (ATG) of the gene to be expressed, will be placed downstream of the transcription start site(s). Any equivalent functional element selected from similar elements in this or other organisms may be used as appropriate in the organism of choice. Equivalent functional elements will include elements with synthetic bases, or elements found in other genes of plants as well as elements found in genes of other unicellular or multicellular organisms.

According to one embodiment of the present invention secretion of the protein out of the cell is preferred. In this embodiment the construct will comprise a signal sequence to effect secretion as is known in the art. A signal sequence that is recognized in the active growth phase will be most preferred. As will be recognized by the skilled artisan, the appropriate signal sequence should be placed immediately downstream of the translational start site (ATG), and in frame with the coding sequence of the gene to be expressed.

Introduction of the construct or vector into the cells is accomplished by any conventional method for transfection, infection or the like, as is known in the art. In constructs comprising a selectable marker the cells may be selected from those bearing functional copies of the construct. If the plasmid comprising the gene of interest is episomal the appropriate selective conditions will be used during growth. Stable transfectants and stable cell lines may be derived from the transfected cells in appropriate cases, in order to conveniently maintain the genotype of interest. Cell growth is accomplished in accordance with the cell type, using any standard growth conditions as may be suitable to support the growth of the specific cell line.

A DNA construct of the present invention can be inserted into the genome of a plant by any suitable method. Suitable plant transformation vectors include those derived from a Ti plasmid of *Agrobacterium tumefaciens*, such as those disclosed by Bevan and Chilton, Ann. Rev. Genetics 16, 357–384, 1982; U.S. Pat. No. 4,940,838 and others. In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, particle gun technology, and transformation using viruses.

The construction of vectors capable of being inserted into a plant genome via *Agrobacterium tumefaciens* mediated delivery is known to those of ordinary skill in the art. Typical plant cloning vectors comprise selectable and scoreable marker genes, T-DNA borders, cloning sites, appropriate bacterial genes to facilitate identification of transconjugates, broad host-range replication and mobilization functions and other elements as desired.

If Agrobacterium mediated delivery is chosen, once the vector has been introduced into the disarmed Agrobacterium strain, the desired plant can then be transformed. Any known method of transformation that will work with the desired plant can be utilized.

Thus, further according to the present invention there are provided a plant cell and a transgenic plant of a species naturally expressing a flavanone-7-O-glucoside-2"-O-rhamnosyl-transferase messenger RNA, such as, but not limited to, grapefruit or pomelo, wherein the plant cell or transgenic plant are genetically modified to include, in an expressible antisense orientation, a nucleotide sequence encoding an antisense RNA molecule being capable of in vivo base pairing with the flavanone-7-O-glucoside-2"-O-rhamnosyl-transferase messenger RNA, to thereby render the flavanone-7-O-glucoside-2"-O-rhamnosyl-transferase messenger RNA, when expressed, amenable to degradation by nucleases present in the plant cell or transgenic plant. The plant cell or transgenic plant according to this aspect of the present invention exhibit either very low or no flavanone-7-O-glucoside-2"-O-rhamnosyl-transferase activity.

It will be appreciated that the nucleotide sequence encoding an antisense RNA molecule being capable of in vivo base pairing with the flavanone-7-O-glucoside-2"-O-rhamnosyl-transferase messenger RNA according to the present invention can be either extrachromosomal or intrachromosomal. In any case, as further detailed herein, the nucleotide sequence is preferably ligated to an expression vector in the antisense orientation downstream to a promoter element and optionally other gene expression control elements.

The nucleotide sequence encoding an antisense RNA molecule being capable of in vivo base pairing with the flavanone-7-O-glucoside-2"-O-rhamnosyl-transferase messenger RNA according to the present invention can be as set forth in SEQ ID NO:20 or a portion thereof longer than 10 nucleotides, preferably longer than 15 nucleotides, more preferably longer than 20 nucleotides, most preferably longer than 30 or 40 nucleotides, so as to ensure specific base pairing with the endogenous flavanone-7-O-glucoside-2"-O-rhamnosyl-transferase messenger RNA produced by the plant cell under physiological conditions.

Alternatively, the nucleotide sequence encoding an antisense RNA molecule being capable of in vivo base pairing with the flavanone-7-O-glucoside-2"-O-rhamnosyl-transferase messenger RNA according to the present invention can share between 80 and 100% identical bases with SEQ ID NO:20 or a portion thereof longer than 10 nucleotides, preferably longer than 15 nucleotides, more preferably longer than 20 nucleotides, most preferably longer than 30 or 40 nucleotides, as determined using a sequence analysis software package developed by the Genetic Computer Group (GCG) at the University of Wisconsin with gap creation penalty of 50 and gap extension penalty of 3, so as to ensure specific base pairing with the endogenous flavanone-7-O-glucoside-2"-O-rhamnosyl-transferase messenger RNA produced by the plant cell.

Still alternatively, the nucleotide sequence encoding an antisense RNA molecule being capable of in vivo base pairing with the flavanone-7-O-glucoside-2"-O-rhamnosyl-transferase messenger RNA according to the present invention can be hybridizable in vitro with SEQ ID NO:20 or a portion thereof longer than 10 nucleotides, preferably longer than 15 nucleotides, more preferably longer than 20 nucleotides, most preferably longer than 30 or 40 nucleotides, under hybridization selected from the group consisting of stringent hybridization, moderate hybridization and mild hybridization, wherein stringent hybridization is effected by a hybridization solution of 6×SSC and 1% SDS, hybridization temperature of 65° C., final wash solution of 0.1×SSC and final wash at 60° C., moderate hybridization is effected by a hybridization solution of 6×SSC and 1% SDS, hybridization temperature of 58° C., final wash solution of 0.5×SSC and final wash at 50° C., whereas mild hybridization is effected by a hybridization solution of 6×SSC and 1% SDS, hybridization temperature of 50° C., final wash solution of 2×SSC and final wash at 40° C., so as to ensure specific base pairing with the endogenous flavanone-7-O-glucoside-2"-O-rhamnosyl-transferase messenger RNA produced by the plant cell. These alternative hybridization conditions are useful in evaluating hybridization capabilities of sequences according to all of the aspects of the present invention. Other hybridization conditions can also be employed. Step by step protocols for the above specified hybridizations and the mentioned other hybridizations are found in *Molecular Cloning*: a Laboratory Manual: 2nd edition, Sambrook et al. 1989, Cold Spring Harbor Laboratory Press, which is incorporated by reference as if fully set forth herein.

Further according to the present invention there is provided a cell genetically modified to include, in an expressible sense orientation, a nucleotide sequence encoding a flavanone-7-O-glucoside-2"-O-rhamnosyl-transferase. The nucleotide sequence according to this aspect of the present invention can be complementary DNA or genomic DNA, and it can be either extrachromosomal or intrachromosomal. It is preferably ligated to an expression vector in the sense orientation and has any of the features described herein above with respect to the isolated polynucleotide according to the present invention. The cell according to this aspect of the present invention can be either a microorganism (either a prokaryote or a eukaryote) or a cell of a multicellular organism, such as a cell of a multicellular plant. In any case, for reasons further detailed hereinunder, the selected cell is preferably capable of producing an activated rhamnose, either in the form of UDP-rhamnose or of dTDP-rhamnose.

Suitable microorganism which are known to produce dTDP-rhamnose include, but are not limited to, Lactobacillus Spp., such as *Lactobacillus caseii* and *Lactobacillus delbrueckeii* and yeast such as *Saccharomyces cerevisiae*.

Cells of suitable multicellular plants include, for example, cells of plants of the genus Citrus, such as, but not limited to, grapefruit and pomelo, both being capable of producing UDP-rhamnose. Additional examples include cells of tobacco (*Nicotiana tabacum*), grapes (*Vitis viniferis*) and carrot (*Daucus carota*).

Further according to the present invention there is provided a plant cell or a transgenic plant of a plant species naturally expressing a flavanone-7-O-glucoside-2"-O-rhamnosyl-transferase, such as, but not limited to, grapefruit and pomelo, the plant cell or transgenic plant being genetically modified to include, in an overexpressible sense orientation, a nucleotide sequence encoding a sense RNA molecule being capable of inducing a co-suppression effect to thereby reduce production of the flavanone-7-O-glucoside-2"-O-rhamnosyl-transferase in the plant cell or the transgenic plant.

The transgenic plants according to the present invention, either expressing the nucleotide sequence according to the present invention as herein described in an antisense form or in an overexpressible sense form, both are characterized by reduced production of flavanone-7-O-glucoside-2"-O-rhamnosyl-transferase. Plants can therefore be selected via taste tests to produce fruits of desired degree of bitterness, to provide, for example, less bitter fruits. Varieties with optimal perceived bitterness levels can be propagated vegetatively by land grafting or other procedures known to the ordinary artisan, and can be used to provide fruits to the fresh fruit market and to produce juices, such as grapefruit juice, that do not require de-bittering.

Furthermore, according to still another aspect of the present invention there is provided a transgenic plant or cell of a plant species naturally expressing a flavanone-7-O-glucoside-2"-O-rhamnosyl-transferase. The transgenic plant or cell is genetically modified to knock-out a gene encoding the endogenous flavanone-7-O-glucoside-2"-O-rhamnosyl-transferase thereof to thereby abolish production of flavanone-7-O-glucoside-2"-O-rhamnosyl-transferase in the transgenic plant or cell.

One ordinarily skilled in the art can readily design a knock-out construct including both positive and negative selection genes for efficiently selecting transfected cells that underwent a homologous recombination event with the construct. Such cells can be cultured and propagated and can further be induced to differentiate into seedlings and grown plants, as well known in the art. Further details concerning uses and procedures of plant gene knock-out are found in Miao et al., 1995; Strepp et al., 1998; and Cooley et al., 1998, which are incorporated by reference as if fully set forth herein.

The flavanone-7-O-glucoside-2"-O-rhamnosyl-transferase gene according to the present invention can be used in a process for enzymatically modifying a 1-6 linkage of hesperidin to a 1-2 linkage of neohesperidin by removing and re-coupling the terminal rhamnose. This is done in a two step process as shown in the left path of FIG. 1. First, hesperidin from orange peels is treated with immobilized commercial hesperidinase to remove the 1-6 linkage. This process is already used commercially as a de-bittering step for citrus juice. The second step involves using a transgenic organism heavily expressing the gene to re-rhamnosylate H7G in the correct 1-2 position. The organism must be capable of naturally producing copious quantities of UDP- or dTDP-rhamnose.

Thus, further according to the present invention, there is provided a commercial process of producing neohesperidin. The process is effected by implementing the following steps, in which, in a first step, hesperidin is obtained, for example, by extraction from a hesperidin producing species of the genus Citrus such as orange. Then, the hesperidin is treated with a hesperidinase, thereby hesperetin-7-glucoside is obtained. Thereafter, the hesperetin-7-glucoside is treated with a flavanone-7-O-glucoside-2"-O-rhamnosyl-transferase in the presence of activated rhamnose, such as UDP-rhamnose or dTDP-rhamnose, and thereby neohesperidin is obtained.

Further according to the present invention there is provided a commercial process of producing neohesperidin dihydrochalcone. The process is effected by implementing the following steps, in which, in a first step, hesperidin is obtained, for example, by extraction from a hesperidin producing species of the genus Citrus such as orange. Then, the hesperidin is treated with a hesperidinase, thereby hesperetin-7-glucoside is obtained. Thereafter, the hesperetin-7-glucoside is treated with a flavanone-7-O-glucoside-2"-O-rhamnosyl-transferase in the presence of activated rhamnose, thereby neohesperidin is obtained. Subsequently, the neohesperidin is treated with an alkali, thereby neohesperidin chalcone is obtained. Finally, the neohesperidin chalcone is reduced, e.g., by a Pd catalyzed H₂ surface reduction process, thereby neohesperidin dihydrochalcone is obtained.

Preferably, the hesperidinase is immobilized on a solid support, whereas the hesperidin is treated with the hesperidinase while passing over the solid support.

Treating the hesperetin-7-glucoside with a flavanone-7-O-glucoside-2"-O-rhamnosyl-transferase in the presence of activated rhamnose is preferably effected in vivo by a cell genetically modified to overexpress the flavanone-7-O-glucoside-2"-O-rhamnosyl-transferase, wherein the cell selected produces activated rhamnose and is capable of intake of the hesperetin-7-glucoside. The neohesperidin in then extracted from the cell. Preferably, the neohesperidin is extracted from the cell prior to the treatment thereof with the alkali. The cell can be of a bacterium, a fungus, a yeast or of a higher plant, as long as it is capable of generating activated rhamnose and is capable of intake of the hesperetin-7-glucoside. The cell can be of a microorganism or of a higher plant. Suitable microorganisms include bacteria and yeast cells. *Lactobacillus casei, Lactobacillus delbrueckeii* and *Saccharomyces cerevisiae* provide good examples for microorganisms. Tobacco (*Nicotiana tabacum*), grapes (*Vitis viniferis*) and carrot (*Daucus carota*) provide good examples for higher plant cells which are readily propagated in culture and qualify with the required criteria.

This aspect of the present invention is of high significance. It is well known that in vitro formation of activated sugar moieties is highly inefficient. Therefore, only when the supply of activated rhamnose is effected in vivo by an organism capable also of intake of hesperetin-7-glucoside, either naturally or rendered capable thereof by physical, chemical, biological or genetic means, and of overexpressing flavanone-7-O-glucoside-2"-O-rhamnosyl-transferase in stoichiometric amounts, would the process described herein be amenable to industrialization.

Further according to the present invention there is provided a method of modifying a rhamnose-1-6-glucose linkage of a chemical compound to a rhamnose-1-2-glucose linkage. The method is effected by implementing the following method steps, in which, in a first step, for removal of the rhamnose group, the chemical compound is enzymatically treated, thereby a first derivative of the chemical compound having a terminal glucose group is obtained. Then, the first derivative is enzymatically treated with recombinant flavanone-7-O-glucoside-2"-O-rhamnosyl-transferase in the presence of activated rhamnose, thereby a second derivative chemical compound having the rhamnose-1-2-glucose linkage is obtained. Enzymatically treating the first derivative with a flavanone-7-O-glucoside-2"-O-rhamnosyl-transferase in the presence of activated rhamnose is preferably effected in vivo by a cell genetically modified to overexpress the flavanone-7-O-glucoside-2"-O-rhamnosyl-transferase, wherein the cell produces activated rhamnose and is capable of intake of the first derivative. The second derivative can be extracted from the cell.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Isolation of a Gene Encoding a Flavanone-7-O-glucoside-2"-O-rhamnosyl-transferase.

Previous attempts to isolate the gene based on purified protein were unsuccessful. These included cDNA library screens using oligonucleotides as well as antibodies. The successful approach, RT-PCR using degenerate primers followed by RACE is described herein.

A cDNA expression library of pomelo young leaves was constructed in Lambda-gt11. Antibodies prepared against pomelo 1-2 rhamnosyl-transferase were used to screen this library. Positive-looking clones were later found to be artifacts in that they did not contain a relevant sequence.

Several oligonucleotides were designed according to the partial peptide sequence and were used to screen the above library by standard techniques. Any resulting clones were irrelevant.

Thus, isolation of the gene encoding flavanone-7-O-glucoside-2"-O-rhamnosyl-transferase (1-2 rhamnosyl-transferase) involved a lengthy process initiated in the purification to homogeneity of the protein, followed by partial peptide sequencing and finalized by cDNA isolation based on RT-PCR and RACE. Details of the process are as follows:

Purification of the enzyme and activity assay: Purification and functional analysis of the flavanone-7-O-glucoside-2"-O-rhamnosyl-transferase protein from young pomelo leaves was as described (Bar-Peled et al. 1991).

Partial peptide sequence of the protein: The purified protein was subject to partial proteolysis, using several different proteases (Lys-C; Asp-N; Trypsin), followed by separation of peptides by SDS-PAGE and blotting on PVDF membranes. Partial peptide sequences generated by Edman degradation were as follows (only conclusive sequence data is given; amino acids in question are not shown): Lys-C cleavage yielded two partial sequences: INYFLHLTA (SEQ ID NO:1) and YPF (SEQ ID NO:2); Asp-N cleavage yielded four partial sequences: IAAILFL (SEQ ID NO:3), YFPSLMGN (SEQ ID NO:4), EKMTIEEA (SEQ ID NO:5) and LFQP (SEQ ID NO:6); whereas, trypsin cleavage yielded a single partial sequence: VVDNGMGMVVPRDK (SEQ ID NO:7)

Isolation of partial cDNA fragments: Partial cDNA fragments were obtained by an RT-PCR approach on target tissue mRNA (young pomelo leaves) using degenerate primers based on the partial peptide sequences. Pomelo young leaf single strand cDNA was prepared by reverse transcription of poly-A RNA using a PCR-adapted poly-T primer (primer contains sequences identical to the −40M13 forward primer followed by 15 T's; see below). PCR was used to amplify gene specific fragments using degenerate primers (designed according to partial peptide sequences; see below) in conjunction with the −40M13 forward primer. Primer sequences were as follows:

Gene specific degenerate primers were: 5'-GAT(C)AAT(C)GGIAT GGGIATGGT-3' (SEQ ID NO:8) for DNGMGMV (SEQ ID NO:9); 5'-GAA(G)AAG(A)ATGACIATT(CA)GAA(G)GAA(G)GC-3' (SEQ ID NO:10) for EKMTIEEA (SEQ ID NO:5); and 5'-AAC(T)TAC(T)TTC(T)CTICAC(T)CTIACIGC-3' (SEQ ID NO:11) for NYFLHLTA (SEQ ID NO:12).

General primers were: PCR-adapted poly-T primer 5'-GTMCCCAGTCACGACGTTTTTTTTTTTTTTT (SEQ ID NO:13); and −40M13 forward primer 5'-GTTTTCCCAGTCACGACG-3' (SEQ ID NO:14).

Amplified DNA fragments were separated and isolated from agarose gels and then cloned into pGEM-T vector (Promega, Madison Wis.). Sequence was obtained by automated sequencing using universal primers (T7 and SP6).

Completion of cDNA sequence: The full length cDNA sequence was obtained after isolating the missing 5' segment by 5'-RACE (Schaefer B.C., 1995) using the following gene specific primers which were derived from the partial cDNA sequence data: RACE1: 5'-CATGCCCATACCATTGTC-3' (SEQ ID NO:15); RACE2: 5'-GACAATGGTATGGG CATG-3' (SEQ ID NO:16); and RACE3: 5'-CCTCAACCACCGAGCCCCAACCAC-3' (SEQ ID NO:17).

Based on the total assembled sequence data, the complete coding region was isolated by RT-PCR using a proof-reading thermostable polymerase (Pfu; Stratagene, La-Jolla, Calif.) and the following primers (each primer contains a cloning adapter sequence; gene specific sequences are underlined): 5'-CATCTAGA<u>ATGGATACCAAGCATCAAG</u>-3' (SEQ ID NO:18); and 5'-CAGGATCC <u>TTATTCAGATTTCTTGACAAG</u>-3' (SEQ ID NO:19).

The resulting translated coding region (1359 base-pairs; FIG. 2, SEQ ID NO:20) contains all partial peptide sequences previously determined by protein sequencing. The sequence of the protein encoded by SEQ ID NO:20 is given in SEQ ID NO:21.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

References Cited

1. Barber, G. A. (1962) The enzyme synthesis of uridine disphosphate L-rhamnose. Biochem. Biophys. Res. Commun 8: 204–209.
2. Bar-Peled, M., E. Lewinsohn, R. Fluhr and J. Gressel. 1991. UDP-rhamnose: flavanone-7-O-glucoside-2-O-rhamnosyl-transferase: purification and characterization of an enzyme catalyzing the production of bitter compounds in citrus. J. Biol. Chem. 266: 20953–20959.
3. Berhow, M. A., and Vandercook C. E. (1989) Biosynthesis of naringin and prunin in detached grapefruit. Phytochemistry 28: 1627–1630.
4. Castillo, J., O. Benavente and J. A. del Rio. (1992) Naringin and neohesperidin levels during development of leaves, flower buds and fruits of Citrus aurantium. Plant Physiol. 99: 67–73.
5. Castillo, J., O. Benavente and J. A del Rio (1993) Hesperetin 7-O-Glucoside and prunin in Citrus species (C. aurantium and C. paradisi). A study of their quantitative distribution in immature fruits and as immediate precursors of neohesperidin and naringin in C. aurantium. J. Agric. Food Chem. 41: 1920–1924.
6. Cooley M. B., Yoder J. L., Insertional inactivation of the tomato polygalacteronase gene. Plant Mol. Biol. 1998, 38: 521–530.
7. Guadagni, D. G. V. P. Maier and J. G. Turnbaugh (1973) Effect of some citrus juice constituents on taste thresholds for limonin and naringin bitterness. J. Sci. Fd Agric. 24: 1277–1288.
8. Horowitz. R. M. and Gentili, B. (1977) Flavonoid constituents of citrus in "Citrus Science and Technology", S. Nagy et al., eds. AVI Publishing Co., Westport, Conn. Vol. 1, pp. 397–426.
9. Horowitz, R. M. and Gentili, B. (1986) Dihydrochalcone sweeteners from citrus flavanones in "Alternative Sweetners", L. O. Nabors and R. C. Gelardi, eds. Marcel Dekker, Inc., NY. pp. 135–153.
10. Jimeno, A., Manjon, A. Canovas, M. and Iborra, J. L. (1987) Use of naringinase immobilized on glycophase-coated porous glass for fruit juice debittering. 13–16.
11. Lewinsohn, E., E. Berman, Y. Mazur and J. Gressel. 1986. Glucosylation of exogenous flavanones by grapefruit (Citrus paradisi) cell cultures. Phytochemistry 25:2531–2535.
12. Lewinsohn, E., E. Berman, Y. Mazur and J. Gressel. 1989a. (7)Glucosylation and (1-6)rhamnosylation of exogenous flavanones by undifferentiated Citrus cell cultures. Plant Science 61:23–28.
13. Lewinsohn, E., L. Britsch, Y. Mazur and J. Gressel. 1989b. Flavanone glycoside biosynthesis in Citrus: chalcone synthase, UDP-glucose: flavanone-7-O-glucosyl-transferase and rhamnosyl transferase activities in cell-free extracts. Plant Physiology 91:1323–1328.
14. Matthews, R. F., Rouseff, R. L., Manlan, M., Norman, S. I. 1990. Removal of limonin and naringin from citrus juice by styrene divinylbenzene resins. Food. Tech. (April) 130–132.
15. McIntosh, C. A. and Mansell, R. L. (1990) Biosynthesis of naringin in Citrus paradisi: UDP-glucosyl-transferase activity in grapefruit seedlings. Phytochemistry, 29: 1533–1538.
16. Miao Z. H., Lam E. Targeted disruption of the TGA3 locus in arabidopsis thaliana. Plant J. 1995, 7:359–365.
17. Naim, M., E. Dukan, U. Zehavi and L. Yaron. (1986) The water—sweet aftertaste of neohesperidin dihydrochalcone and thaumatin as a method for determining their sweet persistence. Chem. Senses. 11: 361–370.
18. Schaefer B. C. Revolutions in rapid amplification of cDNA ends: New strategies for polymerase chain reaction cloning of full-length cDNA ends. Analytical Biochemistry, 1995, 227:255–273.
19. Strepp R., Scholz S., Kruse S., Speth V., Reski R. Plant nuclear gene knockout reveals a role in plastid division for the homologue of the bacterial cell division protein FtsZ, an ancestral tubulin. Proc. Natl. Acad. Sci USA 1998, 95: 4368–4373.

What is claimed is:

1. An isolated polynucleotide comprising a nucleotide sequence encoding a polypeptide having at least 95% sequence identity with SEQ ID NO:21 as determined using a sequence analysis software package developed by the Genetic Computer Group at the University of Wisconsin with gap creation penalty of 12 and gap extension penalty of 4, said polypeptide having a flavanone-7-O-glucoside-2"-O-rhamnosyl-transferase catalytic activity.

2. The isolated polynucleotide of claim 1, wherein said nucleotide sequence is selected from the group consisting of DNA and RNA.

3. The isolated polynucleotide of claim 1, wherein said nucleotide sequence is selected from the group consisting of complementary DNA, genomic DNA and messenger RNA.

4. The isolated polynucleotide of claim 1, further comprising a vector, wherein said nucleotide sequence is ligated to said vector.

5. The isolated polynucleotide of claim 4, wherein said vector is an expression vector, and whereas said nucleotide sequence is operably linked to a promoter sequence.

6. The isolated polynucleotide of claim 5, wherein said nucleotide sequence is ligated to said vector in an orientation selected from the group consisting of a sense orientation and an antisense orientation.

7. The isolated polynucleotide of claim 5, wherein said vector is selected from the group consisting of a vector propagatable in plant cells and a vector propagatable in a microorganism cell.

8. The isolated polynucleotide of claim 5, wherein said nucleotide sequence is as set forth in SEQ ID NO:20.

9. The isolated polynucleotide of claim 1, wherein said polypeptide is as set forth in SEQ ID NO:21.

10. The isolated polynucleotide of claim 1 as set forth in SEQ ID NO:20.

11. The isolated polynucleotide of claim 1, wherein said nucleotide sequence originates from a species of the genus Citrus.

12. A transgenic plant of a species naturally expressing a flavanone-7-O-glucoside-2"-O-rhamnosyl-transferase messenger RNA, wherein the transgenic plant is genetically modified to include an expressible polynucleotide comprising a nucleic acid sequence having at least 95% sequence identity with SEQ ID NO: 20 as determined using a sequence analysis software package developed by the Genetic Computer Group at the University of Wisconsin with gap creation penalty of 50 and gap extension penalty of 3, said polynucleotide designed encoding nucleotide sequences complementary to, and capable of binding to flavanone-7-O-glucoside-2"-O-rhamnosyl-transferase transcripts, and whereas expression of said expressible polynucleotide decreases the level of flavanone-7-O-glucoside-2"-O-rhamnosyl-transferase catalytic activity in said plant cell.

13. The transgenic plant of claim 12, wherein said nucleotide sequence is selected from the group consisting of a complementary DNA and a genomic DNA.

14. The transgenic plant of claim 12, wherein said nucleotide sequence is extrachromosomal.

15. The transgenic plant of claim 12, wherein said nucleotide sequence is intrachromosomal.

16. The transgenic plant of claim 12, wherein said nucleotide sequence is ligated to an expression vector in antisense orientation.

17. The transgenic plant of claim 16, wherein said nucleotide sequence is as set forth in SEQ ID NO:20.

18. A cell genetically modified to include, in an expressible sense orientation, a nucleotide sequence having at least 95% sequence identity with SEQ ID NO: 20 as determined using a sequence analysis software package developed by the Genetic Computer Group at the University of Wisconsin with gap creation penalty of 50 and gap extension penalty of 3, said polypeptide having a flavanone-7-O-glucoside-2"-O-rhamnosyl-transferase activity.

19. The cell of claim 18, wherein said nucleotide sequence is selected from the group consisting of complementary DNA and genomic DNA.

20. The cell of claim 18, wherein said nucleotide sequence is extrachromosomal.

21. The cell of claim 18, wherein said nucleotide sequence is intrachromosomal.

22. The cell of claim 18, wherein said nucleotide sequence is ligated to an expression vector in sense orientation.

23. The cell of claim 22, wherein said nucleotide sequence is as set forth in SEQ ID NO:20.

24. The cell of claim 18, wherein said nucleotide sequence originates from a species of the genus Citrus.

25. The cell of claim 18, wherein the cell is of a microorganism.

26. The cell of claim 25, wherein said microorganism is producing activated rhamnose.

27. The cell of claim 25, wherein said microorganism is selected from the group consisting of Lactobacillus and Saccharomyces.

28. The cell of claim 18, wherein the cell is of a plant species.

29. The cell of claim 28, wherein said plant species is of a genus selected from the group consisting of Citrus, Nicotiana, Vitis and Daucus.

30. A method of modifying a level of a flavanone-7-O-glucoside-2"-O-rhamnosyl-transferase activity in a plant cell, the method comprising regulating the level of activity or expression of a 7-O-glucoside-2"-O-rhamnosyl-transferase mRNA in the plant cell, said 7-O-glucoside-2"-O-rhamnosyl-transferase mRNA comprising a polynucleotide sequence being at least 95% complementary to SEQ ID NO: 20 as determined using a sequence analysis software package developed by the Genetic Computer Group at the University of Wisconsin with gap creation penalty of 50 and gap extension penalty of 3, thereby modifying the level of a 7-O-glucoside-2"-O-rhamnosyl-transferase activity in the plant cell.

31. The method of claim 30, wherein said regulation is upregulation and is effected by expressing within the plant cell an exogenous polynucleotide encoding a polypeptide having at least 95% sequence identity with SEQ ID NO: 21 as determined using a sequence analysis software package developed by the Genetic Computer Group at the University of Wisconsin with gap creation penalty of 12 and gap extension penalty of 4, said polypeptide having 7-O-glucoside-2"-O-rhamnosyl-transferase activity.

32. The method of claim 30, wherein said exogenous polynucleotide comprises a nucleic acid sequence as set forth in SEQ ID NO: 20.

33. A method of producing plant cells having a modified level of flavanone-7-O-glucoside-2"-O-rhamnosyl-transferase, the method effected by:

(a) providing an expressible polynucleotide comprising a nucleic acid sequence having at least 95% nucleic acid sequence identity with SEQ ID NO: 20 operably linked to a plant-operable promoter sequence;

(b) transforming a population of plant cells with said expressible polynucleotide; and (c) selecting a transformed plant cell having a modified level of a flavanone-7-O-glucoside-2"-O-rhamnosyl-transferase activity; and (d) propagating said transformed plant cell having a modified level of a flavanone-7-O-glucoside-2"-O-rhamnosyl-transferase activity;

thereby producing plant cells having a modified level of flavanone-7-O-glucoside-2"-O-rhamnosyl-transferase.

34. The method of claim 33, wherein said selecting is effected by determining in the plant cells at least one parameter selected from the group consisting of taste test of bitterness, flavanone-7-O-glucoside-2"-O-rhamnosyl-transferase catalytic activity, and flavanone-7-O-glucoside-2"-O-rhamnosyl-transferase antigenic activity.

35. The method of claim 33, wherein said nucleic acid sequence having at least 95% nucleic acid sequence identity with SEQ ID NO: 20 is oriented in a sense orientation, and whereas said transformed plant cells have an increased level of flavanone-7-O-glucoside-2"-O-rhamnosyl-transferase activity.

* * * * *